United States Patent [19]

Hitzman

[11] 4,145,445

[45] Mar. 20, 1979

[54] PROCESS FOR PROTEIN PRODUCTION

[75] Inventor: Donald O. Hitzman, Bartlesville, Okla.

[73] Assignee: Phillips Petroleum Company, Bartlesville, Okla.

[21] Appl. No.: 722,196

[22] Filed: Sep. 10, 1976

[51] Int. Cl.$^2$ .............................................. A23K 1/00
[52] U.S. Cl. ...................................... 426/60; 426/62; 426/69; 426/807; 195/27; 195/28 R; 195/49; 195/109
[58] Field of Search ................... 195/1, 27, 28 R, 49, 195/108, 109, 115; 423/352; 426/60, 656, 53, 54, 62, 69, 807

[56] References Cited

U.S. PATENT DOCUMENTS

| 2,965,489 | 12/1960 | Clickner | 426/72 |
|---|---|---|---|
| 3,355,296 | 11/1967 | Perkins et al. | 426/7 |
| 3,384,491 | 5/1968 | Guenther et al. | 426/7 |
| 3,418,208 | 12/1968 | Coty | 195/1 |
| 3,616,224 | 10/1971 | Shiio | 195/49 |
| 3,642,578 | 2/1972 | Hitzman | 195/28 R |
| 3,655,396 | 4/1972 | Goto et al. | 426/60 |
| 3,711,372 | 1/1973 | Donnelly | 195/1 |
| 3,755,082 | 8/1973 | Terui et al. | 195/49 |
| 3,764,476 | 10/1973 | Abe et al. | 195/49 |
| 3,816,250 | 6/1974 | Overbeck et al. | 195/28 R |
| 3,816,256 | 6/1974 | Murata et al. | 195/30 |
| 3,897,303 | 7/1975 | Sherk et al. | 195/27 |

FOREIGN PATENT DOCUMENTS 2790171 7/1973 Australia.
1231058 5/1971 United Kingdom.

OTHER PUBLICATIONS

Rose, "The Condensed Chemical Dictionary", 7th Ed. Van Nostrand Reinhold Co., 1970, p. 603.
Wang, "Proteins from Petroleum", Chem. Engineering, 8/26/68, pp. 99–108 & 158–160.

*Primary Examiner*—R. B. Penland

[57] ABSTRACT

A process for preparing protein which employs an integrated system comprising a fermentation facility, air-separation means, ammonia production means and methanol production means. Microbial cellular material from the fermentor can be employed in feed formulations such that liquid and solid waste disposal in the process is minimal.

18 Claims, 1 Drawing Figure

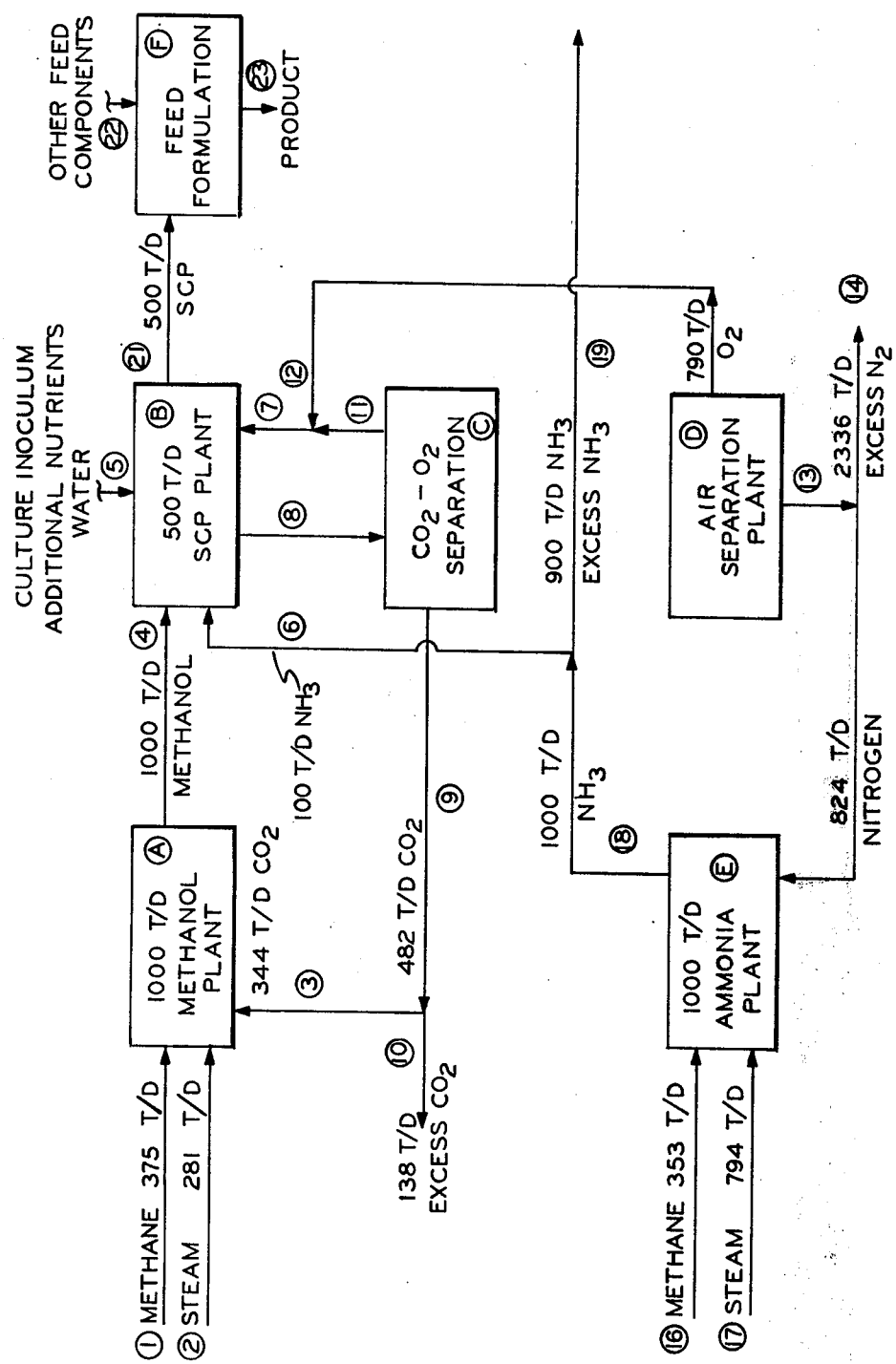

PROCESS FOR PROTEIN PRODUCTION

FIELD OF THE INVENTION

The invention relates to an integrated system for production of feeds suitable for animals including poultry.

BACKGROUND OF THE INVENTION

There is a shortage of available protein for consumption throughout much of the world. The shortage is particularly in the low-cost proteins for both animals and humans. To alleviate protein short-falls, various processes have been developed employing microorganisms wherein biologically produced protein is obtained by the growth of microorganisms of various types on various carbon-containing substrate materials. These methods employ yeasts or bacteria of various types, particularly cultivating such microorganisms on petroleum-derived feedstocks.

Much of the world population has a preference for animal-derived protein materials and, as yet, has little taste for other protein sources, however nutritious and safe. To produce the desired animal proteins, it is necessary to feed animals proteinaceous materials, despite the shortage of available protein, and despite the shortage of natural habitat suitable for grazing and natural development of animals. Thus, the protein shortage cycle, in effect, feeds on itself in much of the world.

SUMMARY OF THE INVENTION

I have developed an integrated system for the production of low-cost single cell proteins wherein my system integrates a methanol production means and an ammonia production means, with separation and recovery of various streams so that waste or loss throughout the system is at a very minimum.

Briefly, natural gas, or other hydrocarbon feed, and steam are converted, together with recycle carbon dioxide from the fermentor, to form a methanol-containing feedstock. The methanol-containing feedstock then becomes the carbon and energy source in my fermentor. Off-gases from the fermentor are separated and at least a portion of the carbon dioxide so obtained is returned to the methanol-producing plant. Nitrogen from an air separation plant, with steam and natural gas or other hydrocarbon, is used in an ammonia-producing plant. The ammonia so produced is important in the fermentor to control pH and to provide nitrogen source material for the microorganisms to assimilate and thus produce the desired protein. The cellular effluent so obtained from my fermentor then can be employed in the formulation of feeds, particularly animal feeds.

BRIEF DESCRIPTION OF THE DRAWING

My invention is illustrated by the attached drawing, but should not be limited by or to the drawing. Steam and methane together with carbon dioxide produced by the fermentation are reacted A to form methanol. Nitrogen, steam, and methane are employed E to produce ammonia. The ammonia and the methanol are employed in a microbial fermentation B to produce a protein-containing product, and carbon dioxide for recycle to the methanol step. The protein-containing product can be incorporated into feed formulations F.

DETAILED DESCRIPTION OF THE DRAWING

A hydrocarbon source such as natural gas or methane 1, steam 2, and carbon dioxide 3 are employed in a methanol-producing plant A. The methanol-containing stream 4 is employed in a fermentation plant B. The fermentation facility B also receives the culture inoculum, additional nutrients such as minerals and growth factors, and water 5; ammonia as nitrogen source 6; and oxygen 7. Off-gases 8 from the fermentor B are taken to a carbon dioxide stripper C. Separated carbon dioxide 9 is returned at least in part to the methanol plant A or purged 10 to other uses. A residue gas stream 11 containing oxygen from stripper C is returned to the fermentor B, together with additional oxygen 12 produced in an air separation plant D. The air separation plant D produces oxygen 12 for use in the fermentor B, and separated nitrogen 13 for use 15 in the ammonia plant E or purged 14. Methane 16 and steam 17 along with nitrogen 15 are used in the ammonia plant E to produce ammonia 18 which is used at least in part 6 in the fermentor B, and can be in part used otherwise 19.

From the fermentor B, the cellular effluent 21 can be employed F in the formulation of products useful in animal feed, receiving such other feed components 22 as necessary to produce a balanced feed formulation 23 as may be suitable or desired for particular animals such as ruminants, swine, or poultry. The formulations can be fed directly in the case of large coordinated feeding facilities, or can be packaged as may be preferred.

Excess carbon dioxide 10 from the $CO_2$ stripper C, if desired, can be combined with part of the excess ammonia 19 to produce urea (not shown), which can be separately used for fertilizer needs, or can as desired be incorporated in feed formulations. Oxygen 12 from the air separation facility D is employed for fermentation, as shown, in fermentor B. The cellular effluent 21 can be treated, such as by centrifugation (not shown), to remove a portion of the liquid containing water-soluble nutrients for recycle (not shown) to the fermentor B and thus reuse a portion of the water-soluble nutrients, and provide a more concentrated feedstream 21 to the feed formulation center F. Cellular effluent 21 can be heat-treated (not shown) to kill the cells prior to formulation of the feeds, if desired. These and other optional features are discussed in detail hereinafter.

Exemplary Material Balance

The following overall material balance as shown on the attached drawing is intended to be illustrative and to assist one skilled in the art to an understanding of my invention, without limiting the scope thereof. The relationships calculated are based on stoichiometric relationships. Of course, actual plant calculations will vary, depending, for example, on cell productivities, rate of carbon and energy source consumption, cell yields, and the like. Particular amounts, sizing, and the like can readily be varied for other situations from the descriptions of each step contained in my disclosure of which this material balance is a part.

Methane (375 tons per day), steam (281 tons per day), and carbon dioxide (344 tons per day) are employed in a methanol-producing facility A to produce methanol at the rate of about 1000 tons/day.

Methane (352 tons per day), steam (794 tons per day), and nitrogen (824 tons per day), are employed in an ammonia-producing facility E to produce ammonia at the rate of about 1000 tons per day, of which about 100 tons per day are employed in fermentor B, and the remainder otherwise employed.

The methanol, about 100 tons per day of ammonia from the ammonia-producing facility E, about 790 tons per day of oxygen from the air separation plant D, preferably with recycle oxygen-containing gases from the $CO_2$ stripper C, and such culture inoculum, additional nutrients, e.g., minerals, and water as needed, are employed in the fermentation facility B under aerobic fermentation conditions to produce a single cell protein product (SCP) at the rate of about 500 tons per day on a nominally dry basis.

The off-gas stream from the fermentor B is treated in the $CO_2$ stripper C to recover the fermentation-produced carbon dioxide at the rate of about 482 tons per day. Of this, about 344 tons per day is recycled to the methanol facility A, and the balance, about 138 tons per day, can be otherwise used, such as for dry ice, or for combination with a part of the excess ammonia for urea production, and the like.

The separation of the $CO_2$ from the fermentor off-gas stream leaves a residue gas stream containing primarily oxygen, and may contain some nitrogen if the oxygen feed to fermentor B is in part air. This residue gas can be recycled to the fermentor, if desired, augmented by additional oxygen from the air separation plant D; or the residue gas can be recycled to the air separation plant D; or wasted. The stream of oxygen-containing gases to the fermentor should be sufficient not only to provide the oxygen necessary for aerobic fermentation conditions, but additionally sufficient to sweep out high contents of $CO_2$ generated by the fermentation which would, unless steadily depleted, tend to inhibit cell growth.

The air separation plant D supplies about 824 tons per day of nitrogen for use in the ammonia facility E, about 790 tons per day of oxygen for use in the fermentation facility B, and excess nitrogen, about 2336 tons per day, which can be used for a variety of other purposes.

The stream containing the SCP product in an amount of about 500 tons per day (nominally dry basis), but including all or most of the fermentation liquid including the trace minerals, is shown employed in a feed formulation facility F in such proportions as suitable and desired for preparing animal feeds, including poultry feeds, of such protein content as may be desired.

Methanol Plant — A

A lower hydrocarbon, such as natural gas, predominantly methane, or substantially pure methane, ethane, or the like, can be converted together with carbon dioxide into a substantially methanol-containing stream.

If the natural gas contains sulfur compounds, treatment by sulfur removal means such as activated carbon beds is desirable, so as to assure that organic sulfur and hydrogen sulfide are adsorbed to avoid possible poisoning of the subsequent catalytic and/or the fermentation processes.

The hydrocarbon gas stream preferably is preheated by heat exchange with hot reformed gas, and mixed with carbon dioxide obtained from the carbon dioxide stripping of vent off-gases from the fermentor. Reaction steam such as at about 30 psig is preheated and mixed with the combined hydrocarbon gas/carbon dioxide stream. The mixture then is reformed employing a suitable catalyst such as a nickel catalyst, to produce reformed gases, CO, $CO_2$ and $H_2$. The reformed gases are cooled, as in a waste heat boiler, compressed to a moderately high pressure such as about 4800 psig, and contacted with a suitable catalyst, operating at about 1500 to 9000 psig, preferably about 5000 psig, pressure, and 250° to 400° C. temperature, such as about 300° C., so as to convert the gaseous stream to methanol at least in part. The catalyst most commonly employed is copper mixed with oxides of zinc, chromium, manganese or aluminum. Unreacted gases can be separated and recycled. Typical conversion is of the order of about 12 to 15 percent per pass. The condensed methanol-containing stream then is employed in my fermentor as a carbon and energy source for the microorganisms.

Alternatively, a synthesis gas can be prepared from natural gas by reacting steam with the methane contained in the natural gas to form a stream containing hydrogen and a mixture of carbon oxides, both carbon monoxide and carbon dioxide. The mixed gas stream thusly obtained would be deficient in carbon for subsequent methanol synthesis, except that, conveniently according to my process, the deficiency can be made up by adding additional carbon dioxide derived from stripping of the off-gases from the fermentor. The additional carbon dioxide preferably is admixed with the natural gas and steam prior to the reforming step such that in effect it promotes a reverse water-gas shift reaction. Stoichiometrically, a hydrogen-carbon monoxide mixture of desired ratio is obtained when the reaction mixture has about three parts methane, one part carbon dioxide, and two parts steam, which endothermic reaction results in a suitable synthesis gas. While natural gas is typified and is preferred when conveniently available, any light hydrocarbon of such as about $C_1$ through $C_4$ is satisfactory, with heavier hydrocarbons requiring proportionately increased amounts of steam to avoid formation of carbon on the catalysts such as promoted nickel catalysts.

The synthesis gas stream generally contains considerable quantities of moisture, and this water can be separated and recycled for steam production, or otherwise used as convenient in the overall process.

These methods can produce substantially pure methanol, though this is unnecessary in the process of my invention, since the methanol stream is not objectionable even though containing varying minor quantities of aldehydes, ketones, acids, and the like.

Fermentation Process — B

The carbon and energy source material in the process according to my invention is a substantially methanol stream, though any of the lower alcohols of about 1 to 4 carbon atoms per molecule can be present; and in the process of preparation of the methanol, various minor amounts of materials such as aldehyde, ketone, acid, or ether substances may also be produced. In my process, it is unnecessary to separate out substantially pure methanol, but rather the process effluent from the alcohol plant can be employed as such, since these other components such as acids, aldehydes, ketones, and ethers are not objectionable. If undesirable amounts of aldehyde are present, then it is a simple matter to add sufficient amounts of ammonia or ammonium compounds, such as ammonium hydroxide, so as to render innocuous the otherwise deleterious aldehyde material in the feedstock. Generally this can be from about 0.01 to 10 mols of the nitrogen-containing compound per mol of aldehyde, though about a 1:1 ratio is to be preferred. The so-added ammonia then becomes a part of the necessary nitrogen source material in the fermentor.

The fermentation process is carried out under conditions effective for aerobic microbial fermentation. Exemplary fermentation temperatures are in the range of about 15° C. to about 65° C., with pressures in the range of about 0.1 to 100 atmospheres, more usually about 1 to 30 atmospheres, and more preferably about 1 to 5 atmospheres, since the higher pressures mean a greater level of dissolved oxygen in the aqueous media and usually higher productivities accordingly.

One of the important parameters to maintaining good cell production is dissolved oxygen level in the fermentor broth. The dissolved oxygen can be increased by operating the fermentor under increased pressures. In general, as the dissolved oxygen level in the fermentor is increased, a direct relationship is observed in that more cells can be grown in a shorter interval of time, at least with the temperature tolerance of the microorganisms. In addition, higher temperatures can be maintained since at higher pressures the microorganisms tend to withstand higher temperatures, and cooling costs thus are reduced somewhat. Fermentation is essentially an exothermic oxidative reaction, and the higher the temperature that can be employed, the less the cooling necessary.

To achieve desired efficiencies, the fermentor is aerated with substantially pure oxygen derived from the liquid oxygen plant hereinbefore mentioned supplemented if desired with recycle oxygen separated from fermentor off-gases, or air. The flow rate of the air or other oxygen stream should be sufficiently great as to sweep out the high contents of carbon dioxide generated in the fermentation process which, if not reduced, could otherwise tend to inhibit cell growth.

Sufficient water is maintained in the fermentation means so as to provide for the particular requirements of the microorganisms employed. Generally, in my process, any microorganisms capable of utilizing a methanol-containing feedstock can be utilized. Among the microorganisms suitable for the types of fermentation described are the bacteria, yeasts, and fungi, such as from the following genera:

Bacteria: Bacillus, Pseudomonas, Protaminobacter, Micrococcus, Arthrobacter, Corynebacterium, Methanomonas, Methylococcus, Methylomonas, Methylobacter, Methylosinus, Methylocystis, Curtobacterium, Acinebacter, Brevibacterium, Nocardia, Mycobacterium, Streptomyces, and Actinomyces.

Yeasts: Candida, Hansenula, Torulopsis, Pichia, Saccharomyces, Rhodotorula, Brettanomyces, and Debaryomyces.

Fungi: Aspergillus, Monilia, Rhizopus, Penicillium, Fusarium, Mucor, Alternaria, Hyphomicrobium, and Helminthosporium.

Exemplary of suitable microorganisms are *Pseudomonas methanica*, which has been assigned the numerical designation NRRL B-3449 by the U.S. Department of Agriculture, Agricultural Research Service, Northern Regional Research Laboratories of Peoria, Illinois; *Pseudomonas fluorescens*, numerical designation NRRL B-3452; *Methanomonas methanica*, numerical designation NRRL B-3450; *Methanomonas methanooxidans*, numerical designation NRRL B-3451; *Arthrobacter parafficum*, numerical designation NRRL B-3453; *Corynebacterium simplex*, numerical designation NRRL B-3454; *Bacillus sp.*, numerical designation NRRL B-8065; and *Bacillus sp.*, numerical designation NRRL B-8066. Combinations of microorganisms also can be employed.

Suitable minerals, growth factors, vitamins and the like generally are added in amounts sufficient to provide for the particular needs of the microorganisms utilized. Minerals and growth factors, and the like, for the microorganisms which are employed vary according to the particular requirements of the microorganisms and are generally known to those skilled in the art or are readily determined by those so skilled.

Nitrogen-containing material can be added in the form of ammonia from the ammonia plant of my overall process. The liquid growth medium, growth factors, minerals, nitrogen source material, and carbon and energy source material in the fermentor then are inoculated with the desired microorganism.

The mineral salts medium employed can be selected from such mediums as are known in the arts depending on the particular microorganism employed. Typically, a suitable medium, FM-12, would include the following:

| One Liter Aqueous Solution | |
| --- | --- |
| Component | Amount |
| $H_3PO_4$ (85%) | 2.0 ml |
| KCl | 1.0 g |
| $MgSO_4 \cdot 7H_2O$ | 1.5 g |
| $CaCl_2 \cdot 2H_2O$ | 0.2 g |
| NaCl | 0.1 g |
| Trace mineral solution | 5.0 ml. |

The trace mineral solution is formulated according to the following recipe:

| One Liter Aqueous Solution | |
| --- | --- |
| Component | Amount |
| $CuSO_4 \cdot 5H_2O$ | 0.06 g |
| KI | 0.08 g |
| $FeCl_3 \cdot 6H_2O$ | 4.80 g |
| $MnSO_4 \cdot H_2O$ | 0.30 g |
| $Na_2MoO_4 \cdot 2H_2O$ | 0.20 g |
| $ZnSO_4 \cdot 7H_2O$ | 2.00 g |
| $H_3BO_3$ | 0.02 g |

Where desired, entering streams to the fermentor can be combined, such as combining the methanol feed with the mineral salts medium. As an optional feature, the fermentor could be fed, continuously, preferably, a mineral salts medium as described above further containing a high concentration of methanol of at least 20 percent, which will sterilize the mineral medium and avoid the necessity of separate sterilization, and at the same time provide convenient means of feeding methanol as the carbon and energy source material.

By maintaining a high input of methanol and proper control of fermentation temperature, pressure, and input of all components, as herein described, it is feasible to obtain relatively high cell densities, e.g., up to 30 grams or more of dry cells per liter, though this is not necessary in my scheme, since either the total fermentor effluent is used in the feed formulation, with the liquid materials providing desirable mineral components and other factors to the feeds; or the fermentor effluent can be partially concentrated and the concentrated SCP-containing liquor so employed, while the separated aqueous phase is recycled to the culturing step.

It is desired for efficiency to maintain a relatively high cell density in the fermentor in my process, to have minimum liquid to be handled in the fermentor effluent, and thus minimum liquid in the animal feed production. This is to be desired whether the fermentor effluent is to be dried and employed as a dried supplement; or whether the liquid fermentor effluent itself is to be admixed as is or partially concentrated with other necessary components, such as crushed grain, in forming a total feed supplement for the animal such as a ruminant.

CO₂ Stripper — C

The off-gases from the fermentor, containing oxygen, carbon dioxide, some moisture of course and, where air is in part employed, also nitrogen and other trace gases, is taken to a stripper where the off-gas stream is stripped of carbon dioxide such as by ethanolamine absorption. The so-recovered carbon dioxide then is employed in part in the methanol synthesis as hereinbefore described, or in part can be combined with a portion of ammonia from the ammonia plant to form urea, which is useful either as a fertilizer or as a ruminant feed supplement. The oxygen separated, together with any other residual gases, can be recycled back to the air separation plant, or can be combined with intake air to the fermentor to provide an oxygen-enriched air supply, as may be convenient. If desired, nitrogen which may be present in the residual gases when air is in part employed in the fermentor, can be separated in the air separation plant and then sent to the ammonia plant.

Air Separation — D

Relatively pure oxygen and nitrogen can be produced by compressing air, optionally with recycle residue gas from the CO₂ stripper, to such as about 4 to 5 atmospheres, and any carbon dioxide and other acidic gases thus present removed by scrubbing with such as a potassium hydroxide solution. The compressed, scrubbed air then can be further compressed to such as about 200 atmospheres, with such cooling as is suitable, and any moisture condensing is removed. The compressed air then is scrubbed by treatment with such as solid KOH or activated alumina. The gas from the last compression stage, such as at about 170° C. and 200 atmospheres, is further cooled to about −30° C. by suitable cooling means, and then subjected to liquefaction/separation as is known in the art to produce, as separate streams, a nitrogen stream containing about 98 weight percent nitrogen by weight and 2 weight percent oxygen by weight and a liquid oxygen stream of about 99 weight percent oxygen and 1 weight percent nitrogen, typically.

Ammonia Production — E

In the ammonia process, natural gas, or other light hydrocarbon, similarly as described for methanol synthesis, is reacted with steam resulting in a mixture comprising carbon monoxide, carbon dioxide, and hydrogen. Carbon dioxide and carbon monoxide are removed, such as by ethanolamine absorption and scrubbing with cuprous ammoniacal solution. These carbon oxides then can be employed as needed in the aforedescribed methanol plant A, or the carbon dioxide can be separated and otherwise used, such as in part combined with excess ammonia not needed by the fermentor so as to produce such as urea.

Nitrogen from the air separation facility and the hydrogen are thereafter converted to ammonia by interreaction at a pressure of such as about 200 to 300 atmospheres, at temperatures of such as about 500° C., for a suitable time, thereby producing the desired amounts of ammonia. Catalysts effective for this purpose include such as iron promoted with small amounts of oxides of aluminum and potassium.

In an alternative partial oxidation mode, natural gas can be partially burned with air, oxygen-enriched air, or oxygen, the natural gas having been previously preheated and compressed to such as about 1000° F. and 350 psig. In this reaction, hydrogen and carbon monoxide are produced. In a second stage shift converter, steam is added, and the carbon monoxide converts substantially to carbon dioxide. The carbon dioxide is removed by a suitable separation means, such as ethanolamine solutions followed by a caustic wash. The carbon dioxide can be separated and used in the methanol synthesis system, or in urea synthesis, or for other purposes. The remaining gas stream is separated to remove nitrogen if present, and the remainder, now substantially pure hydrogen, is contacted with the nitrogen stream from the air separation plant, using a ratio of about 1:3 nitrogen:hydrogen, compressed to such as about 3600 psig, and converted, at about 900° F. over an iron catalyst, to form ammonia.

The ammonia is condensed and employed as needed in the fermentation process as nitrogen source, and for pH control, and excess ammonia can be otherwise employed for various purposes, fertilizer usages, urea production, and the like.

In my system, the ammonia as needed is employed in the fermentation process to supply the nitrogen source material. Optionally, some of the ammonia, and some of the separated carbon dioxide, obtained either from the ammonia plant depending on the process employed or from stripping of carbon dioxide from the vent off-gases from the fermentor, or both, can be combined to form urea. The urea can be used as a fertilizer, or, in part, can be added to the final animal feed formulations. Some of the ammonia can be supplied for fertilizer uses, if desired.

Exemplary Runs

The following runs illustrate exemplary variations from run to run using differing microorganisms as to the oxygen consumption, methanol consumption, cell yields, crude protein in product, productivity, and the like. All of these aspects can vary widely depending on the particular microorganism, various control aspects such as temperature, oxygen input, CO₂ sweepout efficiency, carbon and energy source feed rates, type and efficiency of the fermentor itself, and the like.

| | Comparison of Fermentations | |
|---|---|---|
| Culture | Bacillus sp. NRRL B-8066 | Pseudomonas Methanica NRRL B-3449 |
| Temp. ° C. | 55 | 40 |
| pH | 6.75 | 6.3 |
| MeOH feed conc., % by vol. | 5 | 10 |
| MeOH in effluent, % by vol. | 0.15 | 0–0.5 |
| Dry cell wt (g/l) | 18.8 | 31.85 |
| Calculated Values | | |
| Retention time (hrs) | 2.37 | 2.03 |
| Kg O₂ consumed/kg cells | 1.65 | 2.8 |
| Crude protein (NX6.25), % | 85.6 | 80.6 |
| Cell Yeild, g/100 g MeOH | 47 | 35.7 |
| Kg MeOH/kg Cells | 2.13 | 2.8 |
| Productivity (g/l/hr) | 7.93 | 15.8 |

Feed Formulation — F

The entire fermentor effluent, with relatively high cell densities, e.g., up to such as about 30 grams, or more, cells, dry weight, per liter, then is recovered. Operating the fermentor at elevated pressures is desirable in recovery of metabolic products, since the pressure supply is a driving force for filtration, drum drying if desired; and releasing pressures on the fermentor effluent results in cell rupture, thus releasing cellular components, and consequently a product of enhanced uniformity can be recovered. Pressure release also tends to volatilize any volatile impurities present and enhances the overall efficacy of the process.

The microorganisms in the fermentor effluent can be killed and rendered suitable for feeding by heating to pasteurization temperatures, with or without prior removal of at least a portion of the water from the effluent. Although the pasteurization conditions vary considerably, depending in part on the microorganism, a typical set of pasteurization conditions suitable for use with some microorganisms is about 100° C. for about 30 seconds.

The fermentor effluent contains various fats, carbohydrates, sugars, various salts, vitamins, growth factors, and the like, as well as the protein which is most desired. All of the components of the fermentor effluent are desirable in animal nutrition, and so can become an integral part of the animal feed supplement. This avoids wastage of water-soluble products, proteinaceous materials, nutrients, and the like, which would be lost if only the cellular material was separated out, such as by filtration and the like, and utilized.

The salt content of the fermentor effluent will vary depending on the level of salts maintained for growth purposes. The salts balance analysis of the fermentor effluent would be expected to be close to that of the salts balance of the salts feed to the fermentor. All of the salts normally are needed in animal nutrition, and hence are suitable to become an integral part of the animal feed product. The fermentor effluent also contains a variety of trace amounts of water-soluble proteins, gums, vitamins, and the like, all of which are useful in animal feeds and which otherwise might be lost except for my use of fermentor effluent in animal feeds as an aspect of my process.

According to one aspect of my process, the liquid fermentor effluent containing cells and water-soluble nutrients is conducted from the fermentation means to mixing means wherein dry additives as known to the animal feed arts, such as ground corn, soybean meal, urea, phosphates, limestone, sulfur and the like, are added, and can be formed or extruded into pellets in a ratio to give a correct nutritional balance for the animal feed desired.

A typical trace mineral supplement heretofore commonly added to feed formulations at the rate of about 0.2–0.5 weight percent contains salts wherein the individual components on an elemental basis include:
Manganese — 8.0%
Zinc — 8.10%
Magnesium — 4.18%
Potassium — 6.84%
Iron — 1.30%
Copper — 0.63%
Cobalt — 0.41%
Iodine — 0.60%
Sulfur — 17.05%

Such can be made up as a dry mix, or as aqueous slurry, from appropriate salts, for use in feed formulations.

The fermentor product from the fermentation step of my process, containing the SCP itself plus mineral nutrients used in the fermentation, is advantageously used in the feed formulations since this provides the protein needed as well as the minerals desired. The minerals can be supplemented in the feed, where desired, to add whatever mineral balance is desired, such as with cobalt, etc.

The fermentor effluent not only provides proteinaceous materials and desirable salts, but the liquid fermentor effluent is of a general character such that it provides the necessary binding action so that the feed mixture has a suitable consistency to allow it to be pelletized, prilled or granulated to a size for feeding. The addition of the water-soluble nutrients from the fermentation process reduces the need for additional vitamins and trace elements or water addition of same to the formulated feed mixture.

The feed product can be dried to desired moisture content, usually less than about 10% by weight, for storage, if desired. The feed product can be pasteurized or sterilized by heating to a suitable temperature for a suitable time to maintain storage efficiencies. If the cellular effluent has not been previously heated to kill the cells prior to blending, such heat treatment of the feed formulation also kills the cells as well as making a dryer material or a suitably dry crumb or particle as may be desired for feeding to animals.

As a further example, the following preparation is typical of those which can be employed as a supplemental formulation for cattle feed employing a microbial suspension directly from a fermentor run:

| | |
|---|---|
| Yeast-cell fermentor effluent, including cells and water-solubles, containing, for example, such as about 13 g/l yeast cells (dry basis) | 160 cc |
| Urea | 26 g |
| Soybean meal | 84 g |
| Corn zein | 24 g |
| Limestone | 13 g |
| Sodium chloride | 15 g |

The above is a typical formulation and can be employed as desirable as feed for animals such as cattle. The moist mix described above was made into pills and dried about one hour at about 100° C. Of course, other components could be added where desired, such as molasses, and the like.

Heretofore it would have been desirable to add various trace elements such as potassium, manganese, zinc, magnesium, iron, iodine and copper, and vitamins, such as A and E, to a feed formulation. However, such can be omitted according to my invention, or greatly reduced, since such are present in and have been provided by the water-solubles portion of the single cell protein process effluent.

Alternatively, if desired, the fermentor effluent can be at least partially concentrated by centrifugation to higher cell densities, with recycle of a portion of the spent medium, since the mineral salts are desirable and can be reutilized at least in the fermentation process, and use of the balance including the cellular material in the animal feed formulations.

A typical 32% protein equivalent (PE) commercially available feed supplement now marketed as a liquid feed for animals contains:
35.1% water
5% distillers solubles
40% molasses
8.5% urea
1.5% $(NH_4)_2SO_4$
8.1% 10-34-0
1.5% mineral salts
+ vitamins A suitable comparable formulation can be prepared through my integrated SCP-animal feed process in which the fermentor effluent containing the SCP is recovered without a drying step and with no waste water being produced, while the liquid feed formulation is prepared without the need of additional water. In this aspect, the process is controlled to produce growth of the SCP on methanol at a level of such as about 5 weight % (dry basis) or above yeast or bacterial solids by continuous fermentation. The fermentor effluent is concentrated, such as by centrifugation, to such as about 15 weight % or higher solids content. The resultant rich slurry then can be compounded with other solid components to produce the liquid feed which usually represents about 55–65% solids. The SCP cell rich slurry replaces the distillers solubles, the mineral salts, vitamins, and the water. The final ingredient composition can be balanced to the same formulation as that listed above, or to whatever formula balance is desired.

The remaining separated lean liquor from the concentration step can be cycled back to the fermentor, adding such makeup water, salts, and the like as needed to replace those lost to the rich cellular slurry. The recycle stream can be heated, if desired, for sterilization. Or, the fermentor effluent can be heated to such as about 80° C. for such as about 5 to 15 minutes to kill the cells and thus sterilize the product and recycle. Thus, no waste water from the SCP plant occurs, and no extra water generally is needed in the liquid feed. The high solids contents of the liquid feed supplement normally prevents microbial growth in the product, though a preservative can be added if desired. The SCP is excellent in this usage as it remains suspended and does not settle out as soy protein.

My process substantially results in minimal or no waste effluent from the overall plants, particularly from the feed supplement plant, thus substantially eliminating or minimizing waste treatment facilities required. The fermentor effluent does not have to be dried, but can thusly be employed as a liquid portion in animal feed formulations so that even drying the fermentor effluent is eliminated, and the only drying necessary would be in handling of the feed supplement itself; and this can even be prepared as a liquid stream and fed directly to any feedlot operation tied into the process of my invention.

If desired, the entire fermentor effluent can be dried, such as by vacuum drying or the like, and the entire residue of protein and other cellular products including fermentation salts and the like can be utilized in animal feed supplements or sold as an animal feed supplement.

The separated nitrogen stream from the oxygen plant is used in the production of ammonia which is required in the fermentation. High cell densities and utilization of oxygen from an oxygen plant, together with simple recovery procedures, reduce product costs significantly in addition to eliminating waste disposal facilities. Since the salts employed in the fermentation step itself are all recovered with the product, and are all desirable in the feed supplements, they constitute a plus as to value of the fermentor effluent. My process for optimum operation integrates an oxygen plant, a fermentor, a methanol plant, and an ammonia plant. Substantially the only input to the plants is natural gas or other light hydrocarbon feed such as naphtha, air, water, nutrients such as minerals, and such added feed components as necessary for the animal feed. Products from each step mesh with and are used as feedstocks by other steps, ultimately producing the fermentor effluent which then is employed as such as an animal feed supplement, or concentrated such as by centrifugation to higher cell densities, which high-cell-density material is then used as a feed supplement, and a portion of the nutrient liquid is recycled for reuse.

The disclosure, including data, illustrates the value and effectiveness of my invention. The examples, the knowledge and background of the field of my invention, general principles of the biological and chemical sciences and of other applicable sciences, have formed the bases from which the broad descriptions of the invention, including the ranges of conditions and generic groups of operant components, have been developed, which have formed the bases for my claims here appended.

I claim:

1. A process for the preparation of protein-containing feed materials which comprises the steps of:
    (a) converting a lower hydrocarbon of about 1 to 4 carbon atoms per molecule in a carbon dioxide-utilizing process at least in part to methanol, thereby producing a methanol-containing stream,
    (b) culturing at least one methanol-utilizing microorganism under aerobic fermentation conditions employing said methanol as carbon and energy source, molecular oxygen-containing gases to maintain said aerobic fermentation conditions, assimilable nitrogen source, other nutrients, and water, thereby producing a product stream comprising single cell protein, and an off-gas stream comprising carbon dioxide and unconsumed oxygen,
    (c) separating said off-gas stream into a separated carbon dioxide stream and a residue gas stream containing oxygen,
    (d) recycling said separated carbon dioxide at least in part to said converting step (a),
    (e) recycling said residue gases containing oxygen at least in part to said culturing step (b),
    (f) separating air into streams comprising substantially pure oxygen and substantially pure nitrogen,
    (g) reacting at least a part of said substantially pure nitrogen with hydrogen, thereby forming ammonia,
    (h) feeding at least a part of said ammonia to said culturing step (b) as at least a part of said nitrogen source,
    (i) feeding at least a part of said substantially pure oxygen at least in part to said culturing step (b) as at least a part of said molecular oxygen-containing gases, and
    (j) admixing said product stream, as such or at least in part dewatered, with supplementary feed components, thereby preparing a high-protein feed product.

2. A process for the preparation of protein-containing animal feeds which comprises the steps of:
    (a) converting a lower hydrocarbon of about 1 to 4 carbon atoms with carbon dioxide and steam to produce a reform gas stream comprising carbon monoxide, unreached carbon dioxide, and hydrogen,
    (b) reforming said reform gas stream to produce a methanol-containing stream,
    (c) separating air into streams comprising substantially pure oxygen and substantially pure nitrogen,
    (d) reacting at least a portion of said substantially pure nitrogen with hydrogen, thereby producing ammonia, (e) culturing at least one methanol-utilizing microorganism under aerobic fermentation conditions employing as a carbon and energy source the above-produced methanol, together with molecular oxygen-containing gases at least in part from said air separation, ammonia from said above-produced ammonia as assimilable nitrogen source, other nutrients, and water, thereby producing a product stream comprising single cell protein, and an off-gas stream comprising carbon dioxide and unconsumed oxygen, (f) separating said off-gas stream into a stream of separated carbon dioxide and stream of residue gases comprising oxygen, (g) recycling at least a portion of said residue gases comprising oxygen to said culturing step (e) as a further portion of said molecular oxygen-containing gases, (h) recycling said separated carbon dioxide at least in part to said methanol-producing step (b), and (i) admixing said product stream, as such or dewatered, from said culturing step with supplementary feed components, thereby producing a high protein feed product.

3. The process according to claim 2 further recycling said residue gases to at least one of said culturing step (e) as a portion of said oxygen and said air-separating step (c).

4. The process according to claim 2 wherein said ammonia-forming step (d) comprises (d1) reacting a lower hydrocarbon-containing stream with steam, thereby producing an admixture of carbon monoxide, carbon dioxide, and hydrogen, (d2) separating carbon dioxide and carbon monoxide from said step (d1) as carbon oxides, (d3) recycling said carbon oxides to said methanol producing step (b), and (d4) reacting nitrogrn from an air separation means with said hydrogen, thereby producing said ammonia.

5. The process according to claim 2 wherein said step (a) is a reforming step which comprises reacting a lower hydrocarbon-containing stream with steam and at least a portion of said separated carbon dioxide from said step (h) to form a resultant synthesis gas containing hydrogen, carbon monoxide, and unreacted carbon dioxide; and wherein said reforming step (b) comprises converting said resultant synthesis gas stream to a methanol-containing stream for employment as said carbon and energy source in said culturing step (e).

6. The process according to claim 5 wherein said light hydrocarbon comprises substantially methane.

7. The process according to claim 2 further combining at least a portion of said separated carbon dioxide from said step (f) and at least a further portion of said ammonia from said step (d) to form urea.

8. The process according to claim 7 wherein at least a portion of said urea is incorporated into said feed formulations.

9. The process according to claim 2 further recycling said residue gases from said step (f) at least in part to said culturing step (e).

10. The process according to claim 2 further recycling said residue gases from said step (f) at least in part to said air-separating step (c).

11. The process according to claim 2 comprising the further step of concentrating at least in part said product stream from said step (e) comprising single cell protein, resulting in a concentrated single cell protein stream, and a stream comprising water and a portion of nutrients; and recycling said water and a portion of nutrients to said culturing step (e); and wherein said concentrated single cell protein stream thereafter is employed in said step (i), 12. The process according to claim 2 wherein said methanol-utilizing microorganism is selected from bacteria, yeast, and fungi.

13. The process according to claim 12 wherein said bacteria are selected from the group consisting of Bacillus, Pseudomonas, Protaminobacter, Micrococcus, Arthrobacter, Corynebacterium, Methanomonas, Methylococcus, Methylomonas, Methylobacter, Methylosinus, Methylocystis, Curtobacterium, Acinebacter, Brevibacterium, Nocardia, Mycobacterium, Streptomyces, and Actinomyces; said yeasts are selected from Candida, Hansenula, Torulopsis, Pichia, Saccharomyces; Rhodotorula, Brettanomyces, and Debaryomyces; and said fungi are selected from Aspergillus, Monilia, Rhizopus, Penicillium, Mucor, Alternaria, Hyphomicrobium, and Helminthosporium.

14. A process for the preparation of protein-containing feed supplements which comprises the steps of:
(a) converting a lower hydrocarbon of about 1 to 4 carbon atoms per molecule in a carbon-utilizing process at least in part to methanol, thereby producing a methanol-containing stream, (b) culturing at least one methanol-utilizing microorganisms under aerobic fermentation conditions employing as carbon and energy source said methanol, molecular oxygen-containing gases to maintain said aerobic fermentation conditions, assimilable nitrogen source, other nutrients, and water, thereby producing a fermentation effluent liquor stream comprising single cell protein, and an off-gas stream comprising carbon dioxide and unconsumed oxygen, (c) separating said off-gas stream into a separated carbon dioxide stream, and a residue gas stream comprising oxygen, (d) recycling said separated carbon dioxide stream at least in part to said converting step (a), (e) recycling said residue gases containing oxygen at least in part to said culturing step (b), (f) separating air into streams comprising substantially pure oxygen and substantially pure nitrogen, (g) reacting at least a part of said substantially pure nitrogen with hydrogen, thereby forming ammonia, (h) feeding at least a part of said ammonia to said step (b) as as least a part of said assimilable nitrogen source, (i) feeding at least a part of said substantially pure oxygen at least in part to said culturing step (b) as at least a part of said molecular oxygen-containing gases, (j) concentrating said fermentation effluent liquor stream to produce a rich liquor of increased single cell protein content, and a lean liquor containing a portion of nutrients, (k) recycling said lean liquor as a source in part of said nutrients in said culturing step (b), and (l) admixing said rich liquor with supplementary feed components, thereby preparing a high-protein feed supplement.

15. The process according to claim 14 wherein said methanol-utilizing microorganism is selected from the group consisting of *Pseudomonas methanica* NRRL B-3449; *Pseudomonas fluorescens* NRRL B-3452; *Methanomonas methanica* NRRL B-3450; *Methanomonas methanooxidans* NRRL B-3451; *Arthrobacter parafficum* NRRL B-3453; *Corynebacterium simplex* NRRL B-3454; *Bacillus* sp. NRRL B-8066; and *Bacillus* sp. NRRL B-8065.

16. A process for the preparation of protein-containing feed supplements which comprises the steps of:
   (a) converting a lower hydrocarbon of about 1 to 4 carbon atoms per molecule in a carbon dioxide-utilizing process at least in part to methanol, thereby producing a methanol-containing stream,
   (b) culturing at least one methanol-utilizing microorganism under aerobic fermentation conditions employing as carbon and energy source said methanol, molecular oxygen-containing gases to maintain said aerobic fermentation conditions, assimilable nitrogen source, other nutrients, and water, thereby producing a fermentation effluent liquor stream comprising single cell protein, and an off-gas stream comprising carbon dioxide and unconsumed oxygen,
   (c) separating said off-gas stream into a separated carbon dioxide stream and a residue gas stream comprising oxygen,
   (d) recycling said separated carbon dioxide stream at least in part to said step (a) as at least a portion of said carbon dioxide therein,
   (e) recycling said residue gases containing oxygen at least in part to said step (b) as at least a portion of said molecular oxygen therein,
   (f) separating air into streams comprising substantially pure oxygen and substantially pure nitrogen,
   (g) reacting at least a part of said substantially pure nitrogen with hydrogen, thereby forming ammonia,
   (h) feeding at least a part of said ammonia to said culturing step (b) as at least a part of said assimilable nitrogen source,
   (i) feeding at least a part of said substantially pure oxygen at least in part to said culturing step (b) as at least a further part of said molecular oxygen-containing gases therein,
   (j) concentrating said fermentation effluent liquor stream to produce a rich liquor of increased single cell protein content, and a lean liquor containing a portion of nutrients,
   (k) recycling said lean liquor as a source in part of said nutrients in said culturing step (b), and
   (l) dewatering said rich liquor, thereby preparing a high-protein feed supplement.

17. A process for the preparation of a high-protein product which comprises the steps of:
   (a) converting a lower hydrocarbon of about 1 to 4 carbon atoms per molecule in a carbon dioxide-utilizing reaction at least in part to methanol, thereby producing a methanol-containing stream,
   (b) culturing at least one methanol-utilizing microorganism under aerobic fermentation conditions employing as carbon and energy source said methanol, molecular oxygen-containing gases to maintain said aerobic fermentation conditions, assimilable nitrogen source, other nutrients, and water, thereby producing a fermentation effluent liquor stream comprising single cell protein, and an off-gas stream comprising carbon dioxide and unconsumed oxygen,
   (c) separating said off-gas stream into a separated carbon dioxide stream and a residue gas stream and comprising oxygen,
   (d) recycling said separated carbon dioxide stream at least in part to said converting step (a),
   (e) recycling said residue gases containing oxygen at least in part to said culturing step (b),
   (f) separating air into streams comprising substantially pure oxygen and substantially pure nitrogen,
   (g) reacting at least a part of said substantially pure nitrogen with hydrogen, thereby forming ammonia,
   (h) feeding at least a part of said ammonia to said culturing step (b) as at least a part of said assimilable nitrogen source,
   (i) feeding at least a part of said substantially pure oxygen at least in part to said culturing step (b) as at least a part of said molecular oxygen-containing gases, and
   (j) dewatering said fermentation effluent liquor, thereby preparing a high-protein product.

18. The process of claim 17 wherein said dewatering step (j) comprises drying whereby the resultant product is a dried product comprising substantially nonvolatile materials from said single cell protein process, including salts.

* * * * *